(12) United States Patent
Dedola et al.

(10) Patent No.: US 6,224,577 B1
(45) Date of Patent: May 1, 2001

(54) SYRINGES AND PLUNGERS FOR USE THEREIN

(75) Inventors: Salvatore J. Dedola, New Kensington; Mark W. Hitchins, Sewickley, both of PA (US)

(73) Assignee: Medrad, Inc., Indianola, PA (US)

(*) Notice: Subject to any disclaimer, the term of this patent is extended or adjusted under 35 U.S.C. 154(b) by 0 days.

(21) Appl. No.: 09/033,264

(22) Filed: Mar. 2, 1998

(51) Int. Cl.$^7$ .................................................. A61M 5/00
(52) U.S. Cl. ................................ 604/218; 604/222
(58) Field of Search ............................ 604/218, 219, 604/220, 221, 228, 187, 230, 222

(56) References Cited

U.S. PATENT DOCUMENTS

| | | |
|---|---|---|
| 3,151,617 | 10/1964 | Baum . |
| 4,006,736 | 2/1977 | Kranys et al. . |
| 4,628,969 | 12/1986 | Jurgens, Jr. et al. . |
| 4,677,980 | 7/1987 | Reilly et al. . |
| 4,704,105 | 11/1987 | Adjorjan et al. . |
| 4,718,463 | 1/1988 | Jurgens, Jr. et al. . |
| 5,300,031 | 4/1994 | Neer et al. . |
| 5,383,858 | 1/1995 | Reilly et al. . |
| 5,735,825 | 4/1998 | Stevens et al. . |
| 6,053,895 | 4/2000 | Kolberg et al. . |

FOREIGN PATENT DOCUMENTS

| | | | |
|---|---|---|---|
| 366126 | * | 1/1963 | (CH) .................................... 604/218 |
| 25 14 412 | | 10/1976 | (DE) . |
| 0 027 032 | | 4/1981 | (EP) . |
| 1333235 | * | 6/1963 | (FR) .................................... 604/218 |
| 2 012 590 | | 8/1979 | (GB) . |
| 202402 | * | 3/1966 | (SE) .................................... 604/218 |
| WO 84/02278 | | 6/1984 | (WO) . |

OTHER PUBLICATIONS

International Search Report for Counterpart PCT Application No. PCT/US99/03837.

* cited by examiner

*Primary Examiner*—John D. Yasko
(74) *Attorney, Agent, or Firm*—Gregory L. Bradley

(57) ABSTRACT

The present invention provides a plunger for use in a syringe and a syringe comprising such a plunger. The plunger includes a pressure member extending around the circumference of a generally cylindrical body of the plunger. The pressure member is in substantially sealing contact with the plunger body. The pressure member is sufficiently flexible to be forced radially outwardly to exert force upon the inner wall of the syringe as a result of increased fluid pressure upon forward motion of the plunger. The pressure member thereby forms a substantially sealing engagement with the inner wall of the syringe. In one embodiment, the pressure member comprises a flange attached at a rearward portion of the flange to a body of the plunger. The flange extends forward and radially outward to form a circumferential channel between the flange and the body of the plunger. In another embodiment, the pressure member comprises a resilient O-ring seated in a seating formed around the circumference of the body of the plunger. The seating comprises a ramp portion having a forward radius that is smaller than a rearward radius thereof.

15 Claims, 11 Drawing Sheets

SYRINGES AND PLUNGERS FOR USE THEREIN

FIELD OF THE INVENTION

The present invention relates to syringes and plungers for use therein, and more particularly, to syringes and plungers for use therein in which lubricant need not be applied between the syringe and the plunger.

BACKGROUND OF THE INVENTION

In many medical procedures, such as drug delivery, it is desirable to inject a fluid into a patient. Likewise, numerous types of contrast media (often referred to simply as contrast) are injected into a patient for many diagnostic and therapeutic imaging procedures. For example, contrast media are used in diagnostic procedures such as X-ray procedures (including, for example, angiography, venography and urography), CT scanning, magnetic resonance imaging (MRI), and ultrasonic imaging. Contrast media are also used during therapeutic procedures, including, for example, angioplasty and other interventional radiological procedures. Regardless of the type of procedure, any fluid injected into the patient must be sterile and contain a minimum of pyrogens.

Typically, a fluid is injected into a patient using a manual or powered syringe. Such syringes typically comprise a reciprocally slidable plunger disposed within a cylindrical syringe body.

A number of injector-actuated syringes and powered injectors for use in angiography, computed tomography and NMR/MRI have been developed. In general, syringe plungers for use with such powered injectors require an elastomeric cover which forms a sealing engagement with the inner wall of the syringe barrel. To reduce friction and provide an adequate seal, the syringe barrel, the plunger and the elastomeric plunger cover are typically lubricated during manufacture with, for example, a silicone oil lubricant. U.S. Pat. Nos. 4,628,969 and 4,718,463 describe such lubrication.

The requirement of application of a silicone lubricant oil adds a step in the manufacturing process. Moreover, there is a risk that small amounts of silicone oil can be injected into the patient.

It is desirable to develop a syringe and a plunger for use therein in which an adequate seal is formed therebetween without the need for applying lubrication between the syringe and plunger.

SUMMARY OF THE INVENTION

The present invention provides a syringe and a plunger for use therein for injecting a fluid into a patient. In one aspect of the invention, the plunger comprises a pressure member extending around the circumference of a generally cylindrical body of the plunger. The pressure member is in substantially sealing contact with the plunger body. The pressure member is sufficiently flexible to be forced radially outwardly to exert force upon the inner wall of the syringe in response to increased fluid pressure upon forward motion of the plunger (that is, during an injection procedure). The pressure member thereby forms a substantially sealing engagement with the inner wall of the syringe.

In one embodiment, the pressure member comprises a flange attached at a rearward portion thereof to a body of the plunger. The flange extends forward and radially outward to form a circumferential channel between the flange and the body of the plunger. The flange flexes radially outwardly to form a substantially sealing engagement with the inner wall of the syringe in response to increasing fluid pressure within the channel upon forward motion of the plunger.

In another embodiment, the pressure member comprises a resilient O-ring in sealing contact with the body of the plunger. The O-ring is also preferably in sealing engagement with the inner wall of the syringe. The O-ring is seated in a seating formed around the circumference of the body of the plunger. The seating comprises a ramp portion having a forward radius that is smaller than a rearward radius thereof. The ramp portion thus extends radially outward toward the rear thereof. As the plunger is moved forward, frictional contact with the inner wall of the syringe and increasing fluid pressure force the O-ring to move rearward along the ramp portion of the seating. The increasing radius of the ramp portion causes the O-ring to exert greater force upon the inner wall of the syringe, thereby ensuring a substantially sealing engagement between the O-ring and the inner wall.

The pressure members of the present invention, as compared to conventional designs, maintain a substantially sealing contact with the inner wall of the syringe while reducing frictional forces associated with movement of the plunger within the syringe. Moreover, the pressure members of the present invention maintain substantially sealing contact with the inner wall of the syringe even as the syringe expands under increased pressure (that is, increased fluid pressure during injection).

DETAILED DESCRIPTION OF THE INVENTION

Figure 1:
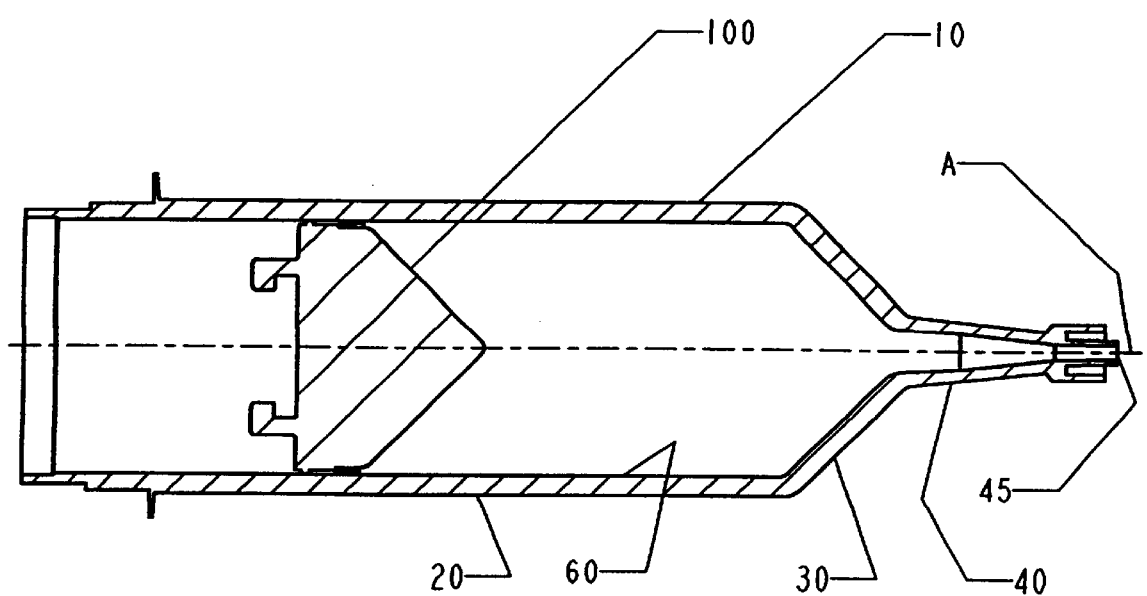
FIG. 1 illustrates a cross-sectional view of a syringe having one embodiment of a plunger of the present invention slidably disposed therein.
Figure 2A:
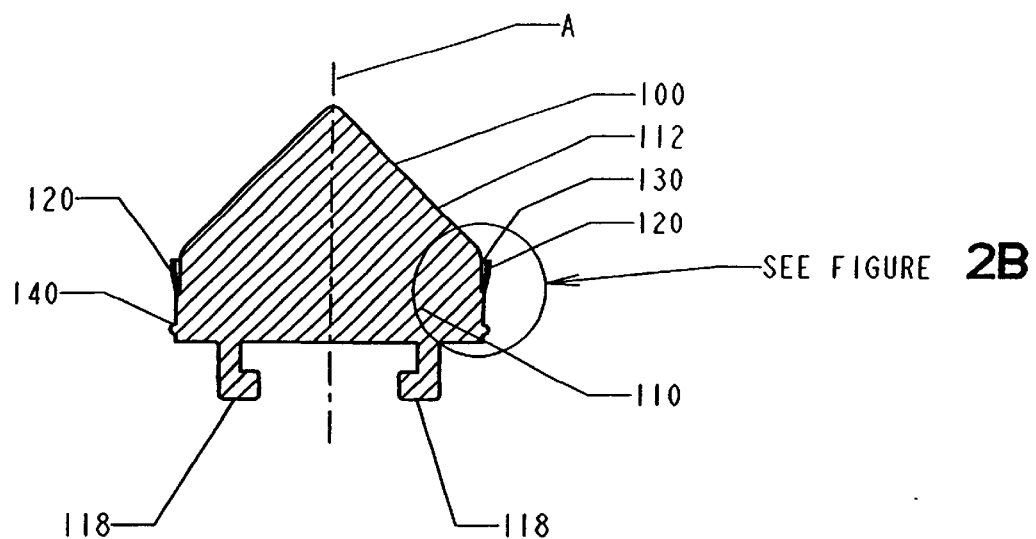
FIG. 2A illustrates a cross-sectional view of the plunger of FIG. 1.
Figure 2B:
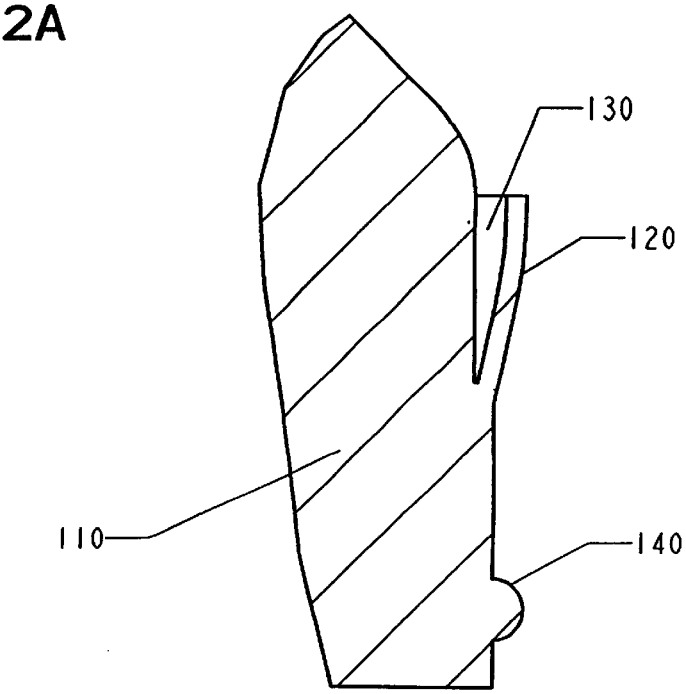
FIG. 2B illustrates an enlarged cross-sectional view of the encircled portion of FIG. 2A.
Figure 3A:
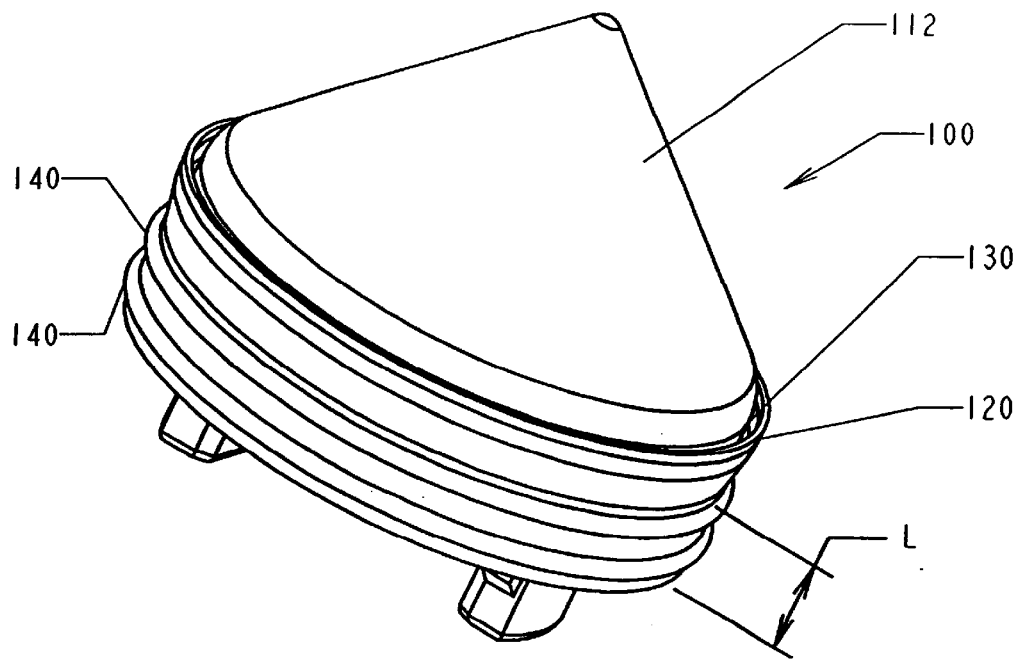
FIG. 3A illustrates a top perspective view of the plunger of FIG. 1.
Figure 3B:
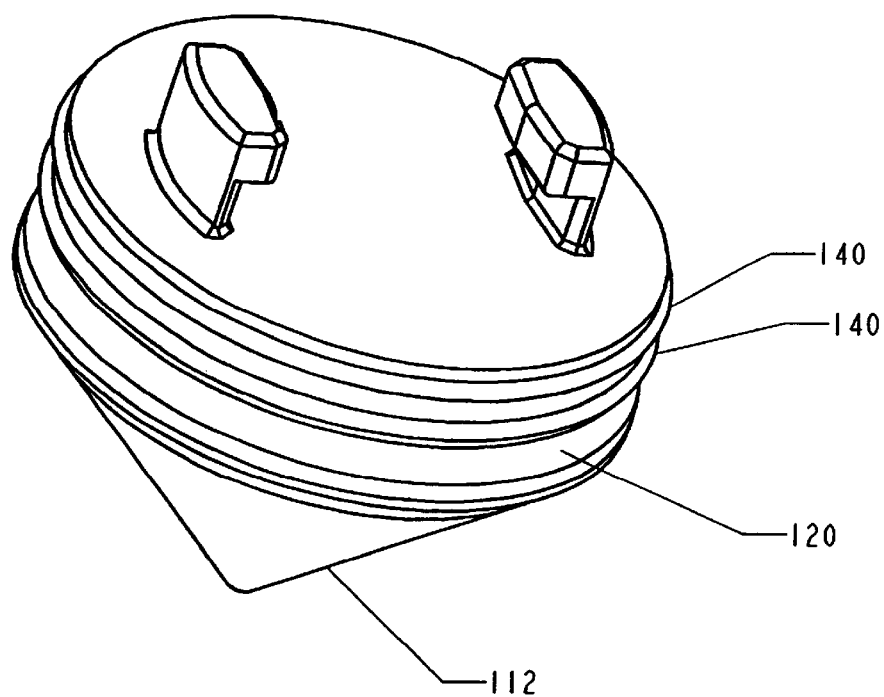
FIG. 3B illustrates a bottom perspective view of the plunger of FIG. 1.

FIG. 1 illustrates a syringe 10 in which a plunger 100 is slidably disposed. In the embodiment of FIG. 1, syringe 10 preferably comprises an elongated, generally cylindrical body or barrel section 20. A generally conical or frusto-conical region 30 is preferably positioned at the forward end of cylindrical body 20. A tapered discharge or injection region 40 is preferably positioned at the forward end of transition region 30. Pressurized injection fluid is discharged from syringe tip 45. As clear to one skilled in the art, however, plunger 100 is suitable for use in generally any type of syringe. Examples of syringes suitable for use in the present invention are disclosed in U.S. Pat. Nos. 4,006,736, 4,677,980, 5,300,031 and 5,383,858, and in U.S. patent application Ser. No. 08/517,645, filed on Aug. 22, 1995, and entitled "Manufacture of Prefilled Syringes" and Ser. No. 08/748,230, filed on Nov. 12, 1996, and entitled "Prefillable Syringes and Injectors for Use Therewith," the contents of which are incorporated herein by reference.

As used herein to describe syringe 10 and plunger 100, the terms "axial" or "axially" refer generally to an axis A around which syringe 10 and plunger 100 are preferably formed (although not necessarily symmetrically therearound). The terms "proximal" or "rearward" refer generally to an axial direction toward the end of syringe 10 opposite syringe tip 45. The terms "distal" or "forward" refer generally to an axial direction toward the syringe tip 45 of syringe 20. The term "radial" refers generally to a direction normal to axis A.

Plunger 100, as best illustrated in FIGS. 1 through 3B, preferably comprises a generally cylindrical body portion 110. To most efficiently expel fluid from syringe 10, the forward portion of plunger 100 is preferably shaped to mate with the forward portion of syringe 10. In that regard, plunger 100 preferably comprises a conical or frusto-conical portion 112 positioned at the forward end of body portion 110. Plunger 100 may also include attachment members 118 adapted to attach to a drive member of a powered injector (not shown).

At least one flexible flange 120 preferably extends around the body portion 110 of plunger 100. Flange 120 is preferably attached to body portion 110 at a rearward end of flange 120. Flange 120 preferably extends radially outwardly (away from body portion 110 and forming an acute angle with the generally cylindrical wall thereof) as it extends forward, thereby forming an annular channel 130 between flange 120 and body portion 110.

During use of syringe 10, fluid within syringe 10 enters annular channel 130. Forward motion of plunger 100 to pressurize and inject fluid contained within syringe 10 results in pressurization of the fluid within annular channel 130. The hydraulic force of the fluid within annular channel 130 forces flange 120 away from body portion 110 and against an inner wall 60 of elongated cylindrical portion 20. As plunger 100 is moved forward, flange 130 is forced against inner wall 60 and prevents any fluid from passing rearward between flange 130 and inner wall 60.

Because plunger 100, unlike currently available syringe plungers, does not rely on elastomeric compression to form a seal with inner wall 60, the force required to advance plunger 100 forward is significantly less than required for currently available plungers. Moreover, the materials for plunger 100 and inner wall 60 can be chosen to have a coefficient of friction less than coefficients of friction common in currently available syringe/plunger combinations. For example, each of plunger 100 and inner wall 60 of syringe 10 can be fabricated from polypropylene to result in a relatively low coefficient of friction. The relatively small force required to advance plunger 100 forward frees plunger 100 and syringe inner wall 60 from the requirement of silicone lubrication required with currently available syringe/plunger combinations. Furthermore, flange 120 maintains a substantially sealing contact with inner wall 60 even as syringe 10 radially expands with increasing pressure during, for example, an injection procedure.

Plunger 100 can be fabricated, for example, via injection molding of a single polymeric material, such as polypropylene. Plunger 100 can also be fabricated, for example, via a coinjection molding process in which a injection moldable elastomer (for example, Santoprene) is injection molded over a harder material (for example, polypropylene or polycarbonate).

As clear to one skilled in the art, the greater the pressure of the fluid within the syringe, the greater the sealing force exerted upon flange 120. At low pressures, however, the radially outward force upon flange 120 may not be sufficient to create a seal adequate to prevent leakage. Moreover, flange 120 may not create a seal adequate to enable drawing of injection fluid into syringe 10 upon rearward movement of plunger 100.

Plunger 100, therefore, preferably further comprises at least one radially outward extending member, such as a rib or ridge 140, positioned rearward of flange 120. More than one ridge 140 (see FIGS. 3A and 3B) may be provided. Ridge(s) 140 preferably extend radially outward a sufficient length to contact inner wall 60 to create a substantially sealing engagement with inner wall 60. Ridge(s) 140 thereby act as a low-pressure seal to prevent injection fluid from leaking rearward when plunger 100 is advanced at low pressure.

Figure 4:
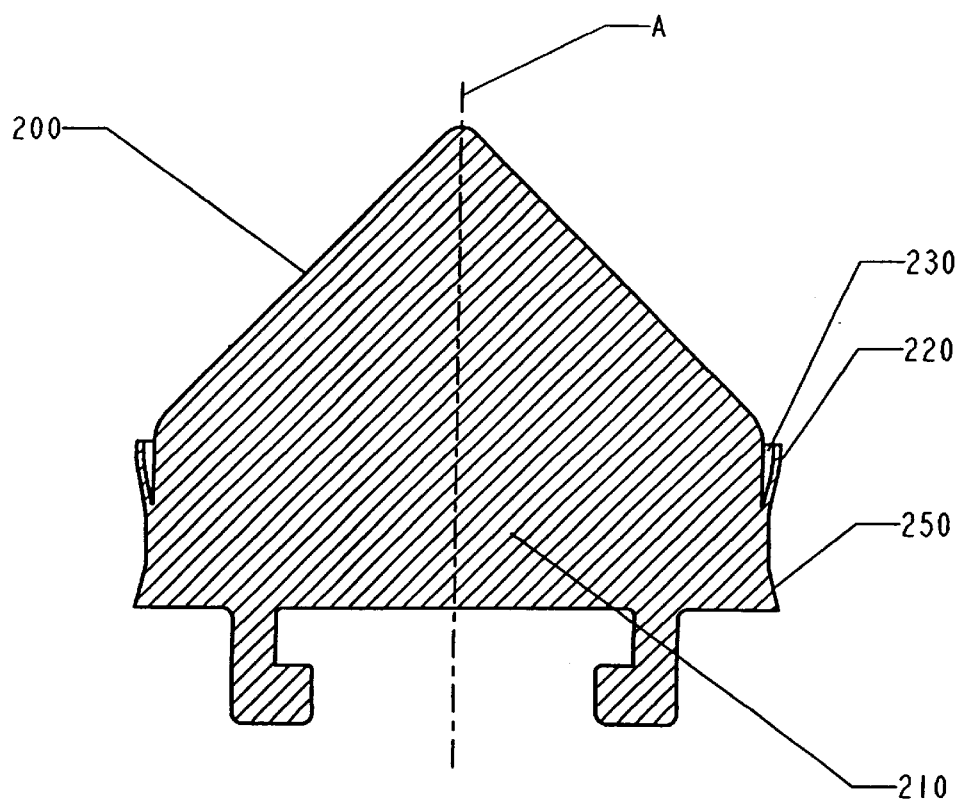
FIG. 4 illustrates a cross-sectional view of another embodiment of a plunger of the present invention.
Figure 5A:
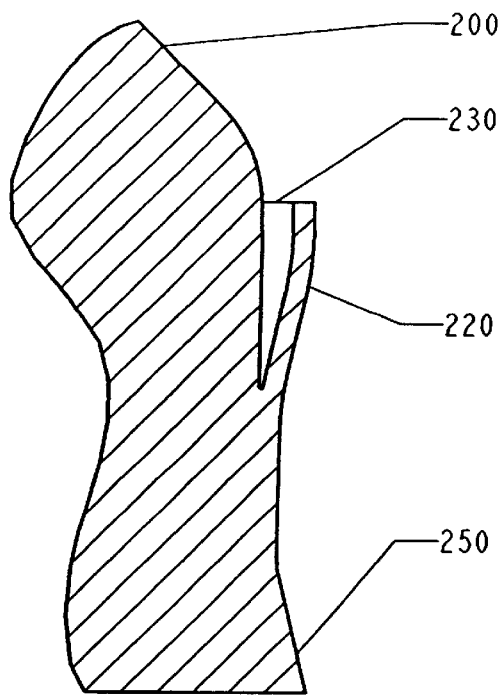
FIG. 5A illustrates an enlarged cross-sectional view of a portion of the plunger of FIG. 4.
Figure 5B:
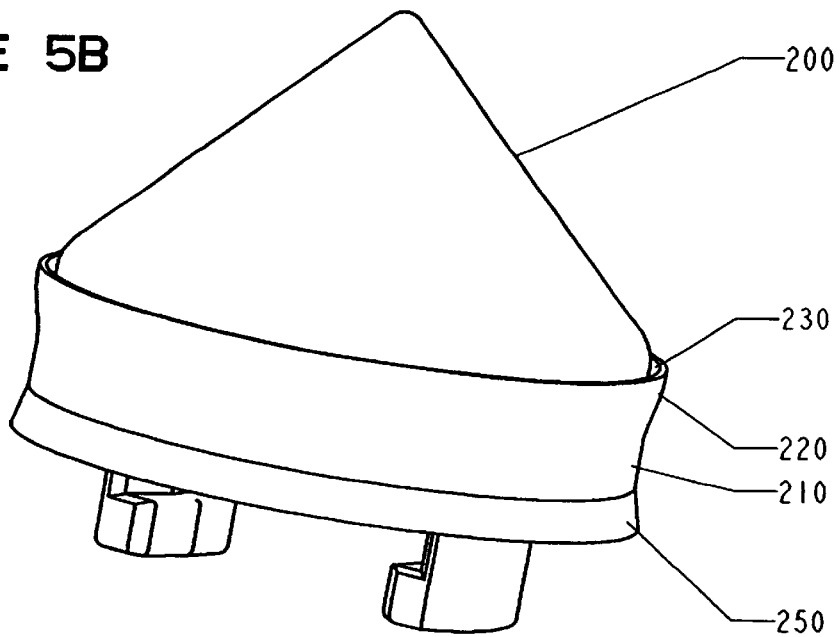
FIG. 5B illustrates a top perspective view of the plunger of FIG. 4.

A low-pressure seal can also be effected by other radially extending members, such as a radially outward flared portion 250 of a plunger 200 illustrated in FIGS. 4 through 5B. Like plunger 100, plunger 200 comprises a flange 220 which extends forward and radially outward from a generally cylindrical portion 210 to create a channel 230. Ridge(s) 140 and flared portion 250 also act to create a seal with inner wall 60 when plunger 100 is moved rearward to draw injection fluid into syringe 10.

Radially outward extending members such as ridge(s) 140 (in connection with flange 120) further act to stabilize plunger 100 to prevent movement of plunger 100 during, for example, an autoclaving or other operation. For this purpose, there may be a plurality of radially extending members positioned at different axial locations on plunger body 110. An axial distance L between the forwardmost sealing edge of the forward radially extending member (or the point at which flange 120 contacts the syringe wall in the case of a single radially extending member) and the rearwardmost sealing edge of the rearward radially extending member is preferably at least 30% of the syringe internal diameter. Such an approximately 3:1 ratio limits rotational movement of the plunger assembly relative to the syringe axis during the autoclave cycle and any other handling.

Figure 6A:
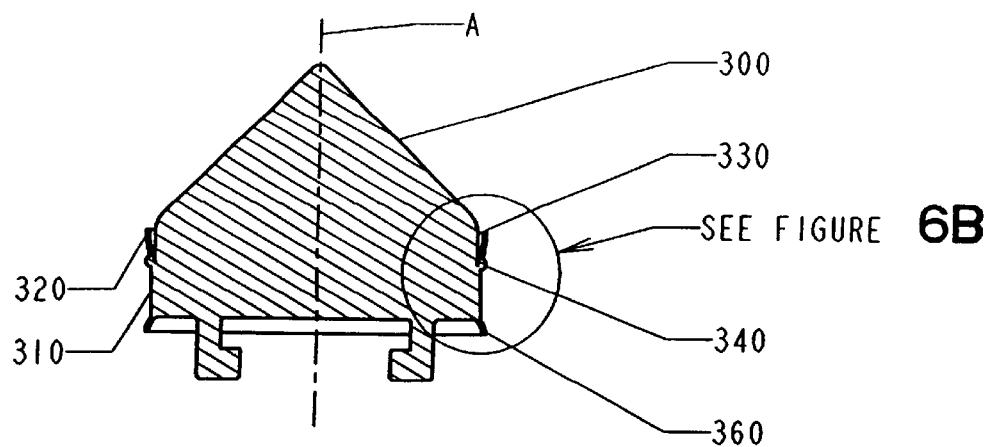
FIG. 6A illustrates a cross-sectional view of another embodiment of a plunger of the present invention.
Figure 6B:
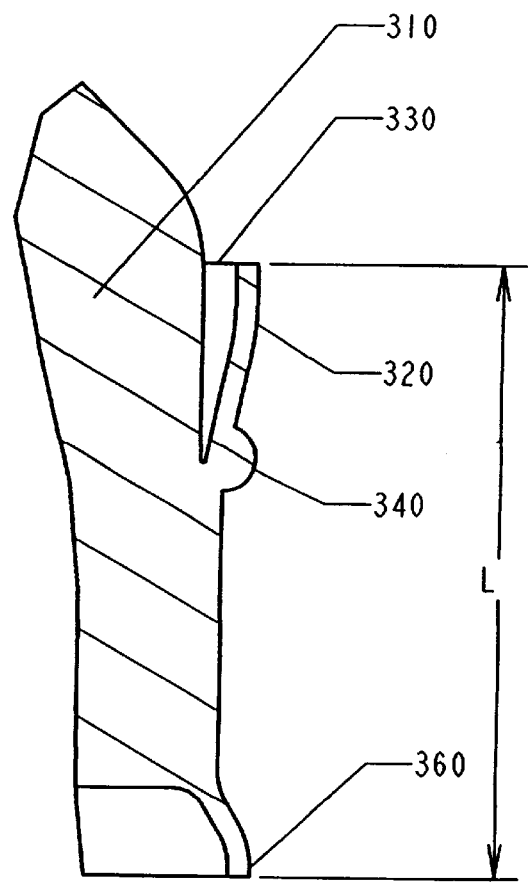
FIG. 6B illustrates an expanded cross-sectional view of the encircled portion of FIG. 6A.

In the case of a plurality of radially outward extending members, the plurality of radially outward extending members can comprise different types of radially extending member. For example, a rib or ridge member can be used in combination with a flared portion. In another embodiment illustrated in FIGS. 6A and 6B, a plunger 300 comprising a flange 320 which extends forward and radially outward from a generally cylindrical portion 310 to create a channel 330. A radially outward extending ridge 340 is preferably positioned at the rearwardmost portion of flange 320 where flange 320 is attached to generally cylindrical portion 310. Ridge 340 acts as a low pressure seal as discussed above. Plunger 300 also comprises a second flange 360 which extends rearward and radially outwardly. Flange 360 is positioned to the rear of ridge 340. Flange 360 is preferably cantilevered rearward and radially outwardly to contact and exert a radially outward force upon the inner wall of the syringe (see FIG. 6C). Flange 360 thereby acts as a wiper seal and provides a contamination barrier. Flange 360 and ridge 340 also act to stabilize plunger 300 in the syringe barrel As described above, an axial distance L' between the contact edge of ridge 340 and the contact edge of the rearward flange 360 is preferable at least 30% of the syringe internal diameter.

Figure 6C:
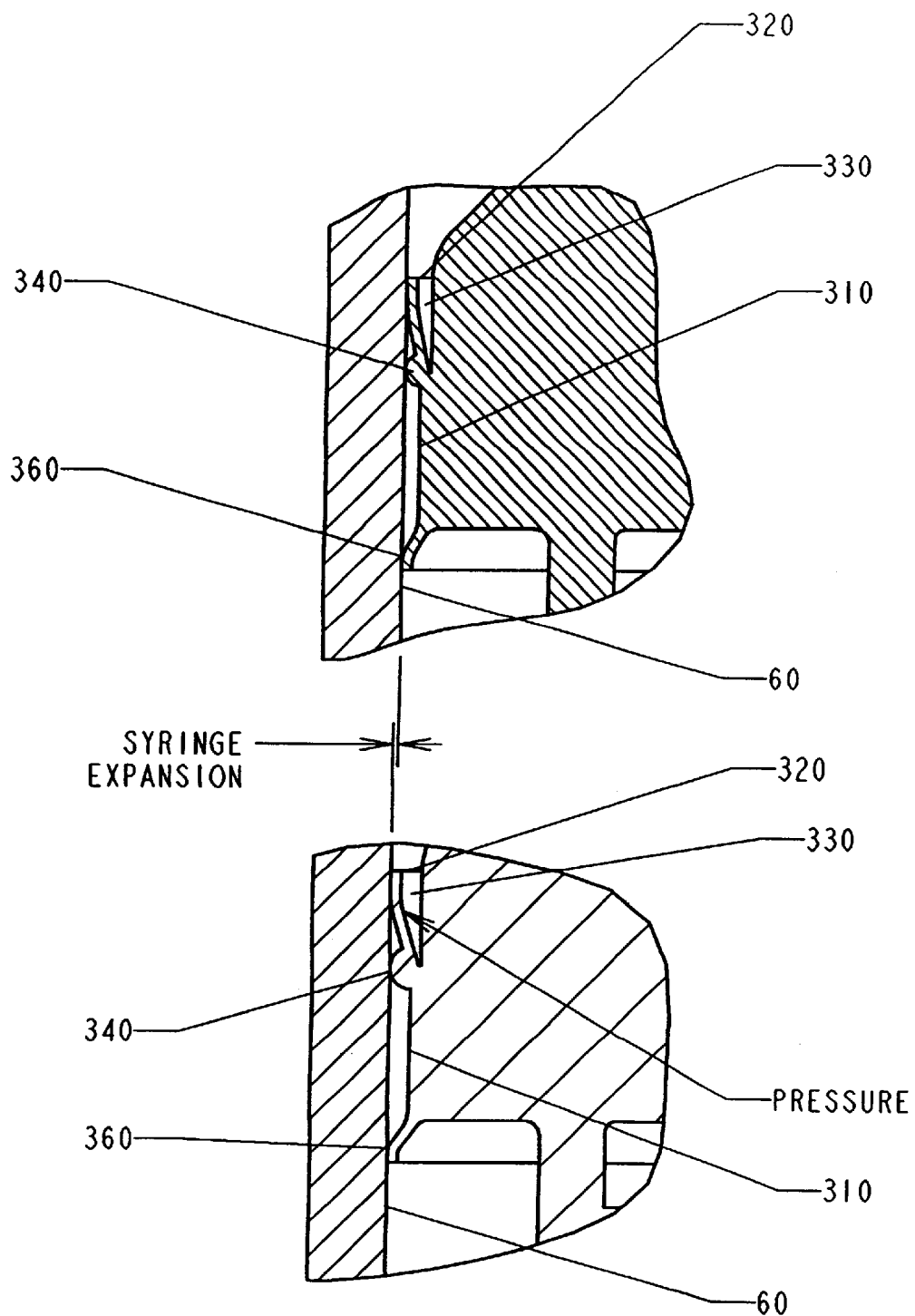
FIG. 6C illustrates an enlarged cross-sectional view of a portion of the plunger of FIG. 6A wherein the syringe has radially expanded and the flanges of the plunger move radially outward to maintain a sealed engagement with the inner wall of the syringe.

As illustrated in FIG. 6C, flange 320, including ridge 340, move radially outward to maintain a substantially sealing contact with inner wall 60 even as syringe 10 radially expands with increasing pressure during, for example, an injection procedure. Likewise, flange 360 preferably also moves radially outward to maintain a substantially sealing contact with inner wall 60 as syringe 10 radially expands.

Figure 7:
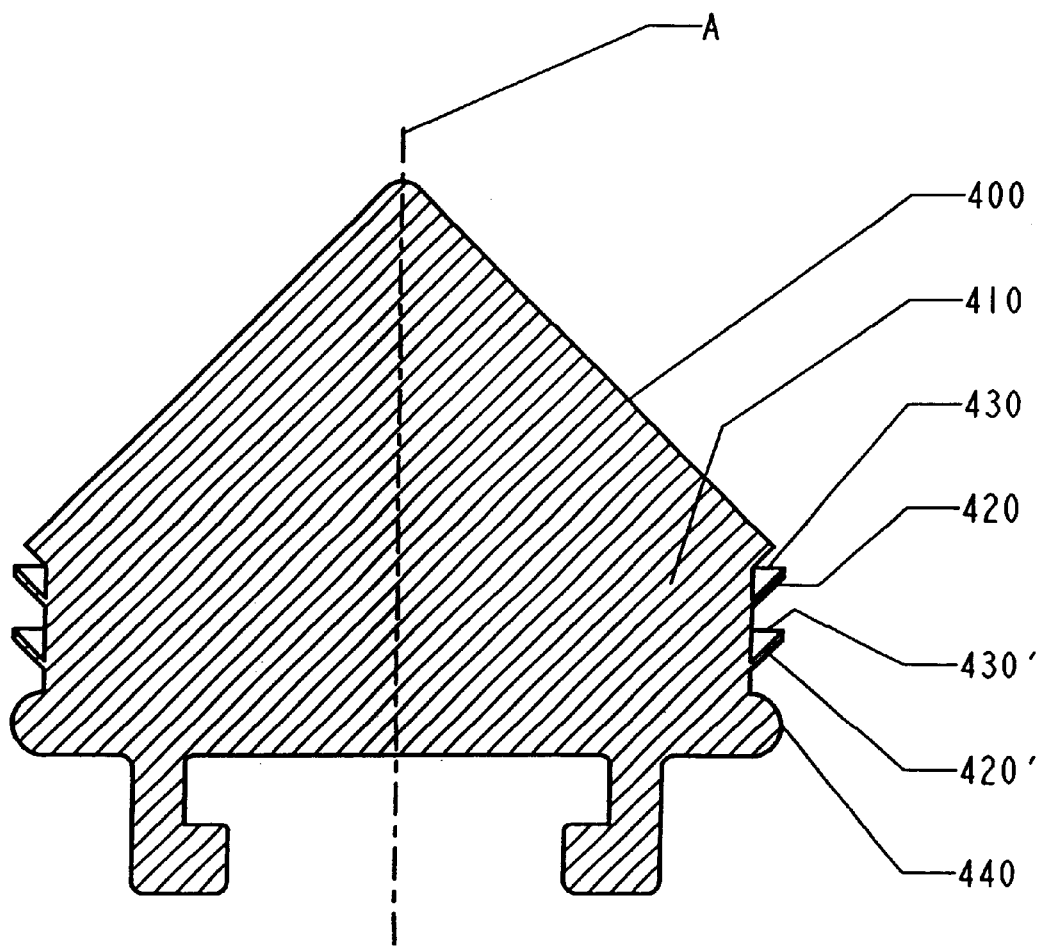
FIG. 7 illustrates a cross-sectional view of another embodiment of a plunger of the present invention comprising two circumferential sealing members.
Figure 8A:
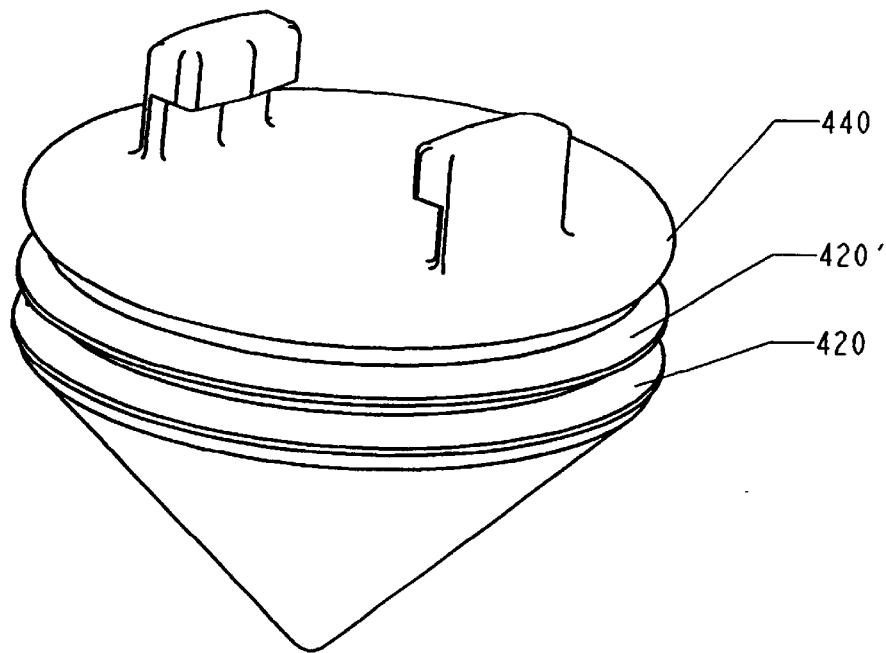
FIG. 8A illustrates a bottom perspective view of the plunger of FIG. 7.
Figure 8B:
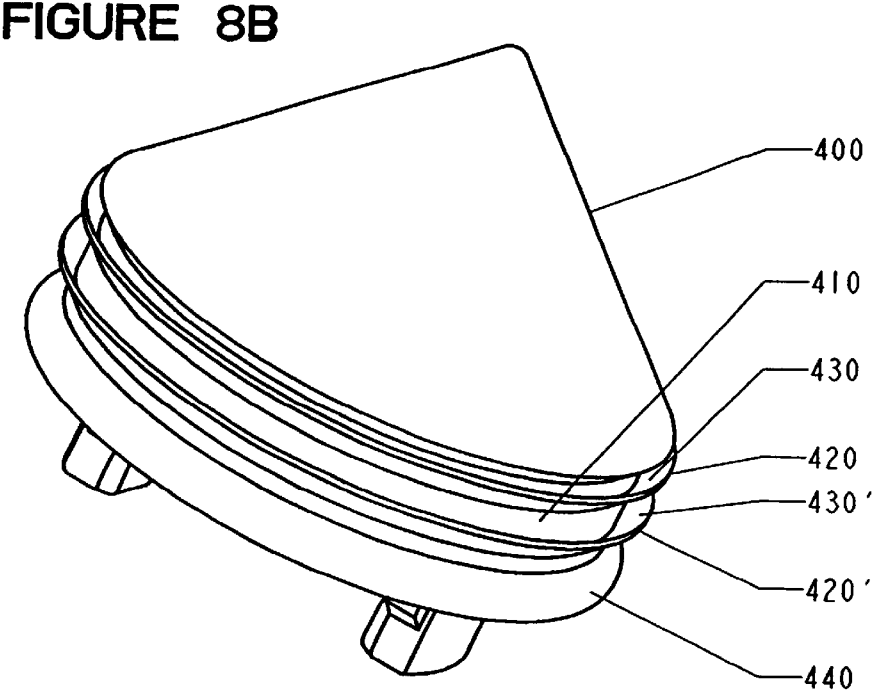
FIG. 8B illustrates a top perspective view of the plunger of FIG. 7.

As illustrated in FIGS. 7 through 8B, a plunger 400 may comprise multiple flanges such as flanges 420 and 420' which extend forward and radially outward from a generally cylindrical portion 410 to create multiple channels 430 and 430', respectively. Typically, only forwardmost flange 420, is pressurized by the fluid within the syringe and thereby forced against the syringe wall to create a high-pressure seal. Flange 420' may act as a backup to flange 420 in this regard, however. Plunger 400 also preferably comprised a rearward, radially outward extending member 440 which functions as a low-pressure seal and (in connection with flanges 420 and 420') as a stabilizing member as described above.

Figure 9A:
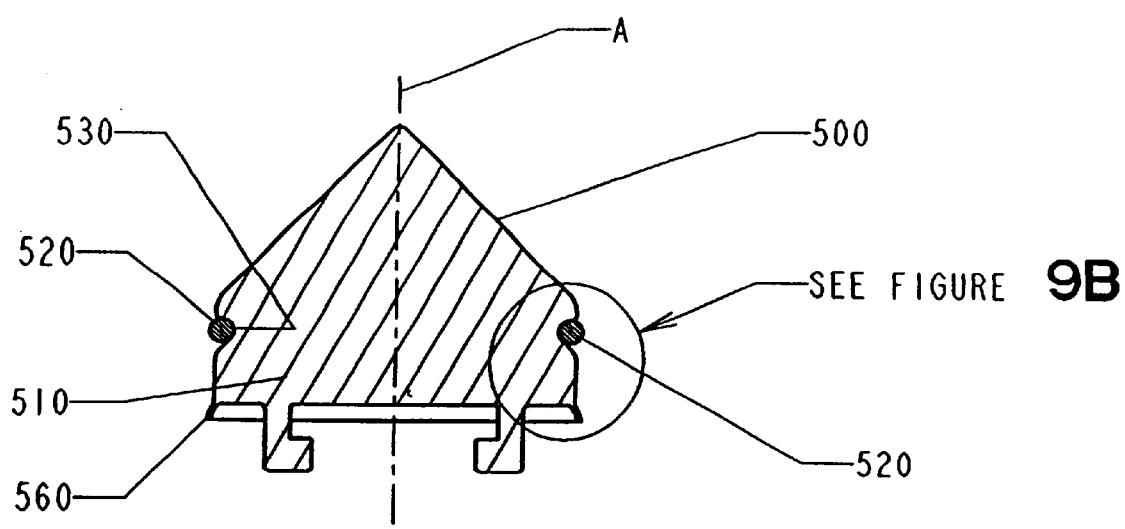
FIG. 9A illustrates a cross-sectional view of another embodiment of a plunger of the present invention.
Figure 9B:
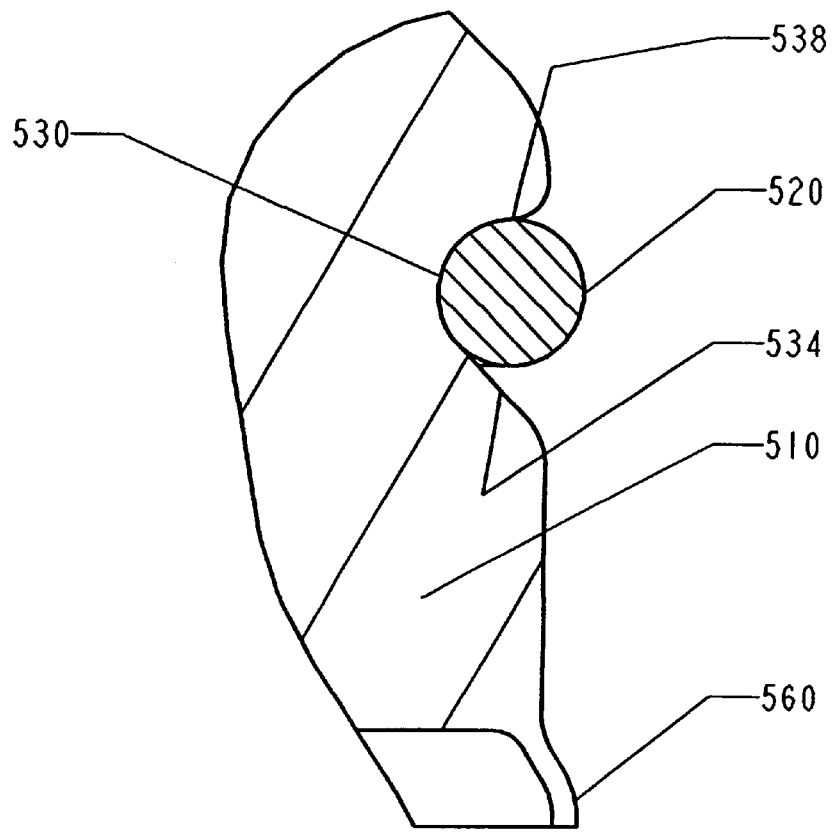
FIG. 9B illustrates an enlarged cross-sectional view of the encircled portion of FIG. 9A.
Figure 9C:
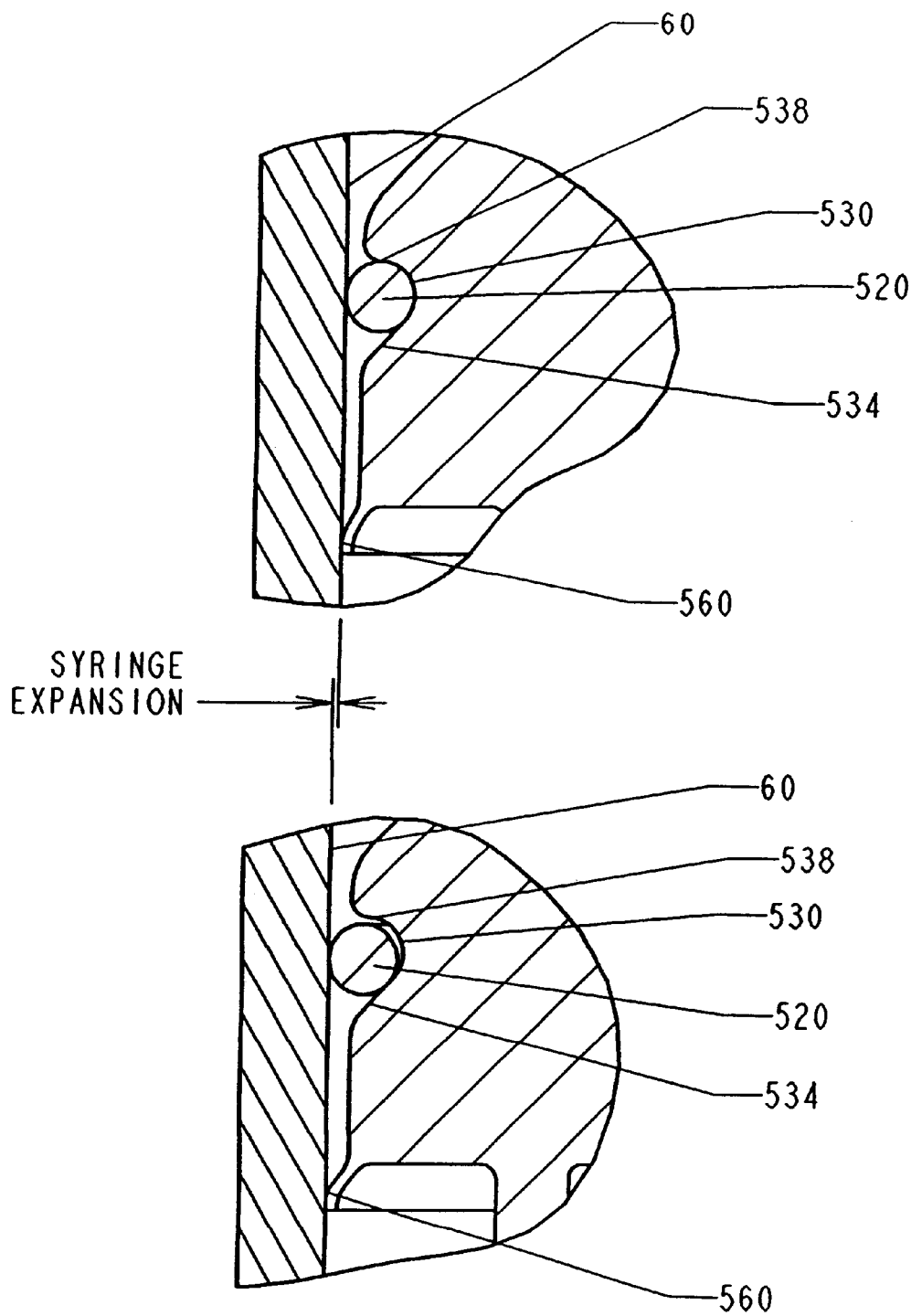
FIG. 9C illustrates an enlarged cross-sectional view of the encircled portion of FIG. 9A wherein the syringe has radially expanded and the O-ring has moved rearward along the ramp portion to maintain a sealed engagement with the inner wall of the syringe.

FIGS. 9A through 9C illustrate another embodiment of the present invention in which a plunger 500 comprises a resilient O-ring 520 in sealing contact with a generally cylindrical body 510 of plunger 500. O-ring 520 is also in sealing engagement with the inner wall of the syringe (not shown). O-ring 520 is seated in a radially inward depression or seating 530 formed around the circumference of body 510. Seating 530 comprises a ramp portion 534 having a forward radius that is smaller than a rearward radius thereof. Ramp portion 534 thus extends or slopes radially outward toward the rear thereof.

As plunger 500 is moved forward, frictional contact with the inner wall of the syringe and increasing fluid pressure force O-ring 520 to move rearward along ramp portion 534 as illustrated in FIG. 9C. The increasing radius of ramp portion 535 causes O-ring 520 to exert greater force upon the inner wall of the syringe, thereby ensuring a substantially sealing engagement between O-ring 520 and the inner wall. Thus, the greater the pressure of the fluid within the syringe, the greater the force exerted by O-ring 520 on the inner wall of the syringe. Furthermore, O-ring 520 maintains a substantially sealing contact with inner wall 60 of syringe 10 even as syringe 10 radially expands under increasing pressure.

Seating 530 preferably further comprises a forward abutment portion 538. Abutment portion 538 retains O-ring 520 with seating 530 during rearward motion of plunger 500.

Plunger 500 also preferably comprises a radially extending member to stabilize plunger 500 as discussed above. For example, plunger 500 may comprise a flange 560, which is preferably positioned at the rearward end of plunger 500. Flange 560 is preferably cantilevered rearward and radially outward to contact and exert a radially outward force upon the inner wall of the syringe. As discussed above, flange 560 thereby forms a substantially sealing engagement with the inner wall of the syringe and acts as a wiper seal to provide a contamination barrier. Flange 560 also acts to stabilize plunger 500 in the syringe barrel. In that regard, the distance between the contact edge of O-ring 520 and the contact edge of flange 560 is preferably at least 30% of the diameter of the inner wall of the syringe.

Although the present invention has been described in detail in connection with the above examples, it is to be understood that such detail is solely for that purpose and that variations can be made by those skilled in the art without departing from the spirit of the invention. The scope of the invention is indicated by the following claims rather than by the foregoing description. All changes to the present invention that fall within the meaning and range of equivalency of the claims are to be embraced within their scope.

What is claimed is:

1. A plunger for use in a syringe, the plunger comprising:
a first, relatively high-pressure member extending around the circumference of the plunger in substantially sealing contact therewith, the first pressure member comprising a forwardmost sealing edge and being sufficiently flexible to be forced radially outwardly to exert force upon an inner wall syringe in response increasing fluid pressure within the syringe during forward movement of the plunger and to compensate for an expansion of the inner wall of the syringe caused by the increasing fluid pressure, the first pressure member thereby forming a substantially sealing engagement with the inner wall of the syringe;
a second, relatively low-pressure member extending radially outward from the plunger at a position rearward from the first pressure member and in substantially sealing engagement with the inner wall of the syringe, the second member being operable to form a relatively low-pressure seal between the plunger and the inner wall of the syringe and to stabilize the plunger within the syringe; and
a third pressure member extending radially outward from the plunger to contact and form a seal with the inner wall of the syringe, the third pressure member comprising a rearwardmost sealing edge and being positioned rearward from the position of the second pressure member, wherein the axial distance between the forwardmost sealing edge of the first pressure member and the rearwardmost sealing edge of the third pressure member is at least 30% of the diameter of the inner wall of the syringe.

2. The plunger of claim 1 wherein the first pressure member comprises a flange attached at a rearward portion thereof to the plunger, the flange extending forward and radially outward to form a channel between the flange and the plunger.

3. The plunger of claim 1 wherein the third pressure member comprises a flange attached to the plunger, the flange being cantilevered rearward and radially outward to form a sealing engagement with the inner wall of the syringe.

4. The plunger of claim 1 wherein the first pressure member comprises a resilient O-ring in sealing contact with the plunger and with the inner wall of the syringe, the O-ring being seated in a seating formed around the circumference of the plunger, the seating comprising a ramp portion having a forward radius that is smaller than a rearward radius thereof, the O-ring being sufficiently resilient to move rearward along the ramp portion of the seating as the plunger is moved forward.

5. The plunger of claim 4 wherein the second pressure member comprises a flange attached to the plunger, the flange being cantilevered rearward and radially outward to form a sealing engagement with the inner wall of the syringe.

6. The plunger of claim 5 wherein the axial distance between the flange and the O-ring is at least 30% of the diameter of the inner wall of the syringe.

7. A syringe comprising a syringe body and a plunger slidably disposed within the syringe body, the plunger comprising a first, relatively high-pressure member extending around the circumference of the plunger in substantially sealing contact therewith, the first pressure member comprising a forwardmost sealing edge and being sufficiently flexible to be forced radially outwardly to exert force upon an inner wall of the syringe body in response to increasing fluid pressure within the syringe during forward movement of the plunger and to compensate for an expansion of the inner wall of the syringe caused by the increasing fluid pressure, the first pressure member thereby forming a substantially sealing engagement with the inner wall of the syringe;

a second, relatively low-pressure member extending radially outward from the plunger at a position rearward from the first pressure member and in substantially sealing engagement with the inner wall of the syringe, the second member being operable to form a relatively low-pressure seal between the plunger and the inner wall of the syringe and to stabilize the plunger within the syringe; and a third pressure member extending radially outward from the plunger to contact and form a seal with the inner wall of the syringe, the third pressure member comprising a rearwardmost sealing edge and being positioned rearward from the position of the second pressure member, wherein the axial distance between the forwardmost sealing edge of the first pressure member and the rearwardmost sealing edge of the third pressure member is at least 30% of the diameter of the inner wall of the syringe.

8. The syringe of claim 7 wherein the first pressure member comprises a flange attached at a rearward portion thereof to the plunger, the flange extending forward and radially outward to form a channel between the flange and the plunger.

9. The syringe of claim 5 wherein the third pressure member comprises a rearward flange attached to the plunger, the rearward flange being cantilevered rearward and radially outward to form a sealing engagement with the inner wall of the syringe body.

10. The syringe of claim 7 wherein the first pressure member comprises a resilient O-ring in sealing contact with the plunger and with the inner wall of the syringe body, the O-ring being seated in a seating formed around the circumference of the plunger, the seating comprising a ramp portion having a forward radius that is smaller than a rearward radius thereof, the O-ring being sufficiently resilient to move rearward along the ramp portion of the seating as the plunger is moved forward.

11. The syringe of claim 10 wherein the second pressure member comprises a flange attached to the plunger, the flange being cantilevered rearward and radially outward to form a sealing engagement with the inner wall of the syringe body.

12. The syringe of claim 11 wherein the axial distance between the flange and the O-ring is at least 30% of the diameter of the inner wall of the syringe body.

13. A syringe comprising a syringe body and a plunger slidably disposed within the syringe body, the plunger comprising:

a first pressure member extending around the circumference of the plunger in substantially sealing contact therewith, the first pressure member being sufficiently flexible to be forced radially outwardly to exert force upon an inner wall of the syringe body in response to increasing fluid pressure within the syringe during forward movement of the plunger and to compensate for an expansion of the inner wall of the syringe caused by the increasing fluid pressure, the first pressure member thereby forming a relatively high-pressure seal with the inner wall of the syringe;

a second pressure member extending radially outward from the plunger at a position rearward from the first pressure member and in substantially sealing engagement with the inner wall of the syringe, the second member operable to form a relatively low-pressure seal between the plunger and the inner wall of the syringe and to stabilize the plunger within the syringe; and a third pressure member extending radially outward from the plunger to contact and form a seal with the inner wall of the syringe, the third pressure member being positioned rearward from the second pressure member;

wherein the first pressure member comprises a resilient O-ring in sealing contact with the plunger and the inner wall of the syringe, the O-ring being seated in a seating formed around the circumference of the plunger, the seating comprising a ramp portion having a forward radius that is smaller than a rearward radius thereof, the O-ring being sufficiently resilient to move rearward along the ramp portion of the seating as the plunger is moved forward.

14. The syringe of claim 13 wherein the third pressure member comprises a flange attached to the plunger, the flange being cantilevered rearward and radially outward to form a sealing engagement with the inner wall of the syringe.

15. The syringe of claim 13 wherein the first pressure member comprises a flange attached at a rearward portion thereof to the plunger, the flange extending forward and radially outward to form a channel between the flange and the plunger.

* * * * *